June 15, 1954 E. S. BOERNER Plant Pat. 1,284
ROSE PLANT
Filed May 13, 1953
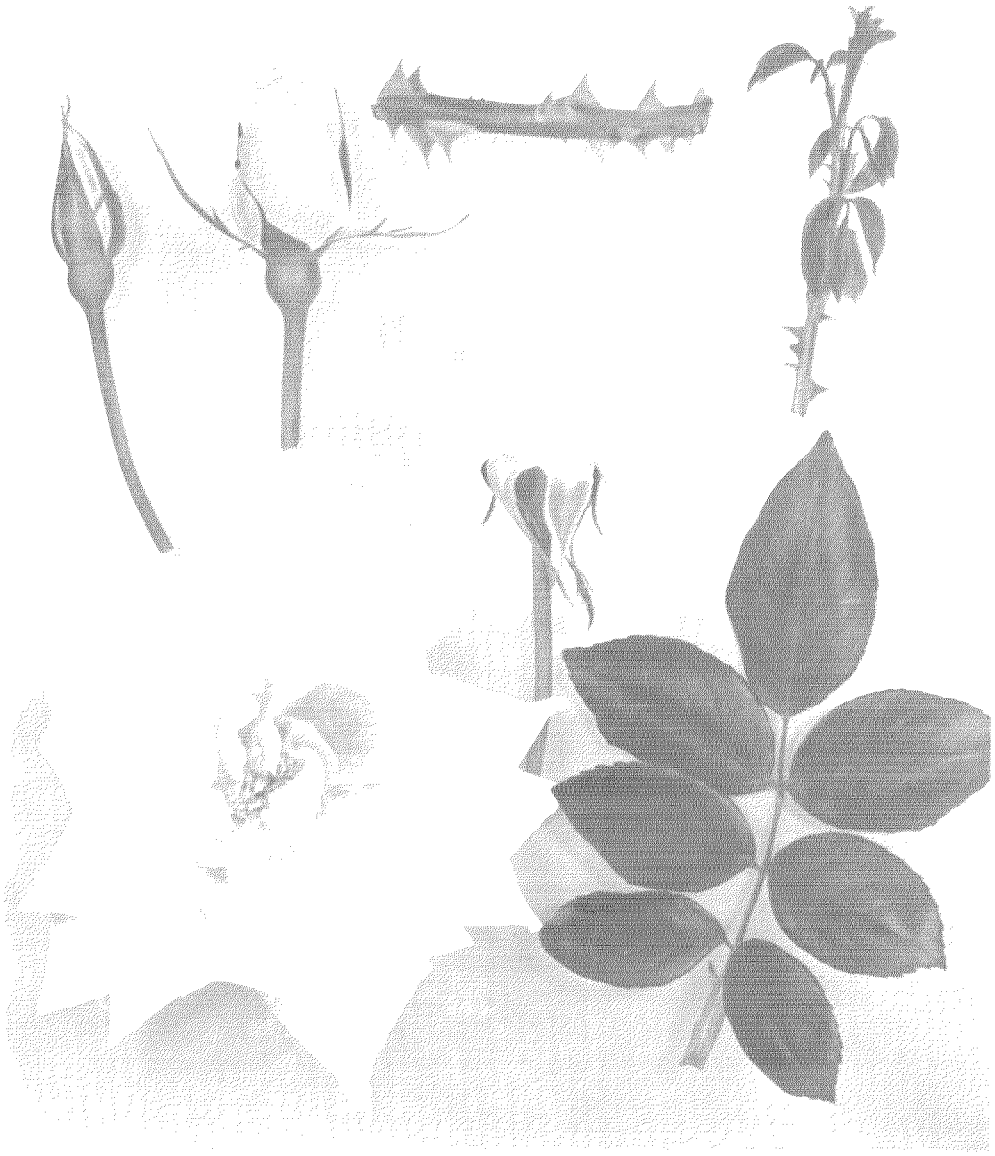
Inventor
E. S. Boerner
By Robb & Robb
Attorneys Patented June 15, 1954

Plant Pat. 1,284

UNITED STATES PATENT OFFICE 1,284

ROSE PLANT

Eugene S. Boerner, Newark, N. Y., assignor to Jackson & Perkins Company, Newark, N. Y., a corporation of New York Application May 13, 1953, Serial No. 354,902

1 Claim. (Cl. 47—61)

The present invention relates to a new and distinct variety of rose plant of the hybrid tea class, which was originated by me by crossing the variety "Mandalay" (Plant Patent No. 775) with the variety "Golden Scepter" (Plant Patent No. 910).

The primary objective in making this cross was to produce a new variety of rose plant of the large-flowered, yellow hybrid tea type. This objective was fully achieved by using the variety "Mandalay" as one of the parents, this variety being the largest-flowered hybrid tea rose, and by using the variety "Golden Scepter" as a base for the more intensive color.

As a result of the aforementioned breeding, my new variety is definitely distinguished from its parents, as well as from all other varieties of its class, as evidenced by the following unique combination of outstanding characteristics:

(1) The Golden Yellow general color tonality of the flowers, which may be specifically described as Pinard Yellow, lightly overcast with Apricot Yellow, and the retention of the coloring throughout the entire life of the flowers;

(2) The great size of the flowers, with perfect form and slow, symmetrical unfolding habit;

(3) The unique characteristic arrangement of the stamens which are very decorative when the flowers are fully open; and (4) The shiny and decorative foliage which is proportional to and well-balanced with the large size of the flowers.

Asexual reproduction of my new variety by budding at Newark, New York, and at Pleasanton, California, shows that the foregoing characteristics and distinctions come true to form and are established and transmitted through succeeding propagations.

The accompanying drawing shows typical specimens of the flowers, foliage and stems of my new variety in different stages of development, as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
*Seed parent.*—"Mandalay."
*Pollen parent.*—"Golden Scepter."
Classification:
*Botanic.*—Hybrid tea.
*Commercial.*—Hybrid tea.

*Flower*

(Observations made in a greenhouse at Newark, New York, in the early morning in the month of December.)

Blooming habit: Recurrent—continuous.
Bud:
*Size.*—Very large.
*Form.*—long, pointed; is not affected by wet or hot weather.
*Color.*—When sepals first divide—Cadmium Yellow, Plate 3. When petals begin to unfurl—Deep Chrome, Plate 3. When half blown: inside of petals—Empire Yellow, Plate 4, lightly overcast with Apricot Yellow, Plate 4; Reverse of petals—Empire Yellow, Plate 4.
*Sepals.*—Slightly branched; curl back when petals begin to unfurl. Color: inside—Olivine, Plate 32; outside—Cress Green, Plate 31.
*Calyx.*—Color—Cress Green, Plate 31. Shape—apple. Size—broad. Aspect—smooth. Odor when rubbed—none.
*Peduncle.* — Length — medium. Aspect—prickly. Strength—erect; heavy. Color—Bice Green, Plate 17.
*Opening.*—Opens well; is not affected by adverse weather conditions.
Bloom:
*Size.*—Very large; average size when fully expanded—7½ inches.
*Borne.*—Singly.
*Stems.*—Long; strong.
*Form.* — When first open — high center. Permanence—retains its form to the end; outer petals curl back.
*Petalage.*—Double (full but open center); number of petals under normal conditions—35.
*Color.*—Center of flower—Deep Chrome, Plate 3. Outer petals—Pinard Yellow, Plate 4. Base of petals (aiglet)—Lemon Chrome, Plate 4. Inside of petals—Pinard Yellow, Plate 4, lightly overcast with Apricot Yellow, Plate 4. Reverse of petals—Naphthalene Yellow, Plate 16, lightly overcast with Pinard Yellow, Plate 4. General tonality from a distance—Pinard Yellow, Plate 4.
*Discoloration.*—General tonality at end of first day—Pinard Yellow, Plate 4, lightly overcast with Apricot Yellow, Plate 4. Second day—Pinard Yellow, Plate 4. Third day—Pinard Yellow, Plate 4, lightly overcast with Naphthalene Yellow, Plate 16.

Petals:

*Texture.*—Thin; is not affected by wet or hot weather.

*Appearance.*—Inside—satiny; outside—shiny.

*Form.*—Oval; slightly notched.

*Arrangement.*—Imbricated (regularly arranged shingle-like).

*Petaloids in center.*—Few; large.

*Persistence.*—Drop off cleanly.

*Fragrance.*—Moderate. Nature—tea (average hybrid tea scent).

*Lasting quality.*—On the plant—long. As cut flower—long.

*Genital organs*

Stamens, anthers: Large; many; mixed with petaloids. Color—Deep Chrome, Plate 3.

Stamens, filaments (threads): Very long; make an interesting circle in the center of the flower. Color—Apricot Yellow, Plate 4.

Pollen: Color—Maize Yellow, Plate 4.

Styles: Bunched; uneven length; short; thin.

Stigmas: Color—Martius Yellow, Plate 4.

Ovaries: All enclosed in calyx.

Hips: None.

Seeds: None.

*Plant*

Form: Bush.

Growth: Vigorous; upright.

Foliage: 5 to 7 leaflets.

*Size.*—Large.

*Quantity.*—Normal.

*Color.*—New foliage: Upper side—Lettuce Green, Plate 5, overcast with Hay's Russet, Plate 14; under side—Absinthe Green, Plate 31, lightly overcast with Hay's Russet, Plate 14. Old foliage: upper side—Dusky Yellowish Green, Plate 41; under side—Bice Green, Plate 17.

*Shape.*—Oval-pointed.

*Texture.*—Upper side—glossy; under side—smooth.

*Ribs and veins.*—Prominent.

*Edge.*—Serrated (saw-toothed).

*Serration.*—Single; small.

*Leaf stem.*—Color—Light Bice Green, Plate 17. Under side—smooth.

*Stipules.*—Medium length; slightly bearded.

Wood:

*New wood.*—Color—Oil Green, Plate 5. Bark—smooth.

*Old wood.*—Color—Cress Green, Plate 31. Bark—smooth.

Thorns:

*Thorns.*—Quantity—on main stalks from base—many; on laterals from stalk—many. Form—broad base; long; some straight and some hooked downward. Color when young—Eugenia Red, Plate 13. Position—irregular.

*Prickles.*—On main stalks—none. On laterals—none.

*Short needles.*—On main stalks—none. On laterals—none.

I claim:

A new and distinct variety of rose plant of the hybrid tea class, substantially as herein shown and described, characterized particularly as to novelty by the Golden Yellow general color tonality of its flowers and the retention of their coloring throughout their entire life, by the relatively large size and perfect form of its flowers and their slow and symmetrical unfolding habit, by the distinctive and decorative arrangement of the stamens when the flowers are fully open, and by its well-proportioned and well-balanced shiny and decorative foliage.

No references cited.